United States Patent [19]

Brodt et al.

[11] Patent Number: 5,292,957
[45] Date of Patent: Mar. 8, 1994

[54] PROCESS FOR THE PREPARATION OF N-ALKYLHALOGENOANILINES

[75] Inventors: Werner Brodt, Eppstein/Taunus; Theodor Papenfuhs, Frankfurt am Main, both of Fed. Rep. of Germany

[73] Assignee: Hoechst Aktiengesellschaft, Frankfurt am Main, Fed. Rep. of Germany

[21] Appl. No.: 778,163
[22] PCT Filed: Jul. 2, 1990
[86] PCT No.: PCT/EP90/01003
§ 371 Date: Feb. 20, 1992
§ 102(e) Date: Feb. 20, 1992
[87] PCT Pub. No.: WO91/00262
PCT Pub. Date: Jan. 10, 1991

[30] Foreign Application Priority Data

Jun. 30, 1989 [DE] Fed. Rep. of Germany ........ 3921447

[51] Int. Cl.$^5$ ............................................. C07C 209/26
[52] U.S. Cl. ...................................... 564/417; 564/431
[58] Field of Search ..................... 564/398, 431, 417

[56] References Cited

U.S. PATENT DOCUMENTS

| | | | |
|---|---|---|---|
| 3,350,450 | 10/1967 | Dovell et al. | 260/577 |
| 3,541,153 | 11/1970 | Sandridge | 260/577 |
| 3,803,054 | 4/1974 | Habig et al. | 252/439 |

FOREIGN PATENT DOCUMENTS 2941070  4/1981  Fed. Rep. of Germany .

OTHER PUBLICATIONS

Dovell et al. J. Amer. Chem. Soc. 87:2767-8 (Apr. 1965).

*Primary Examiner*—Glennon H. Hollrah
*Assistant Examiner*—Brian M. Burn

[57] ABSTRACT

A process for the preparation of N-alkylhalogenoanilines of the formula (I)

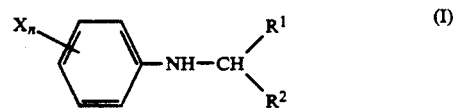

in which X is a chlorine or bromine atom and n is the number 1 or 2, $R^1$ is an alkyl ($C_1$-$C_4$) radical, $R^2$ an alkyl ($C_1$-$C_6$) radical or $R^1$ and $R^2$ together with the carbon atom can form a five- or six-membered cycloalkane ring, by reacting a halogenonitrobenzene of the formula (II)

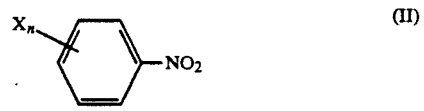

in which X and n have the abovementioned meanings with an at least stoichiometric amount of a carbonyl compound of the formula (III)

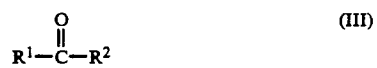

in which $R^1$ and $R^2$ have the meanings mentioned or $R^1$ and $R^2$ together with the carbon atom of the carbonyl group can form a five- or six-membered cycloalkane ring, in an inert organic solvent at temperatures of about 10 to about 100° C., at a hydrogen superatmospheric pressure of about 0 to about 50 bar, in the presence of a platinum catalyst on activated carbon.

7 Claims, No Drawings

PROCESS FOR THE PREPARATION OF N-ALKYLHALOGENOANILINES

The present invention relates to an ecologically and economically improved process for the preparation of N-alkylhalogenoanilines by reductive alkylation of nitrohalogenobenzenes, in particular the preparation of N-isopropyl-4-chloroaniline by reductive alkylation of p-nitrochlorobenzene with acetone in the presence of a sulfited platinum catalyst of defined specific activity.

The problem of halogen elimination which occurs in the catalytic hydrogenation of halogen-containing nitro aromatics is also especially important in reductive alkylations of halogen-containing nitro or amino aromatics, in particular in industrial processes.

There has therefore not been a lack of attempts to avoid the disadvantages which occur in reductive alkylation of halogen-containing nitro aromatics or anilines, such as halogen elimination, ring hydrogenation or polyalkylation.

The prior art closest to the process according to the invention is described in German Offenlegungsschrift 2,941,070 A1. The process described there comprises reacting a halogenoaniline or halogenonitrobenzene with 1 to 10 equivalents of an aliphatic carbonyl compound in an inert solvent, but preferably in a solution of the halogenoaniline or of the nitro aromatic in the aliphatic carbonyl compound, using 0.05 to 2.0% by weight of a sulfited platinum/carbon catalyst at temperatures of 70 to 120° C., preferably at 80° to 100° C. The hydrogen superatmospheric pressure employed in this process is 40 to 100 bar. The yields of N-halogenoalkylanilines are about 95% of theory at a purity of mostly over 98%.

"Virtually no halogen elimination is observed" in this process, although no analytical investigations of halogen elimination are mentioned.

The closest prior art furthermore includes the process described in U.S. Pat. No. 3,350,450 for the preparation of aromatic amines by catalytic hydrogenation of aromatic nitro compounds, in particular of N-alkylhalogenoanilines by reductive alkylation of halogenoanilines or halogenonitrobenzenes in a one- or two-stage process, using hydrogen and aliphatic aldehydes or ketones in the presence of palladium, platinum, rhodium, ruthenium or cobalt sulfides.

In the abovementioned U.S. patent, the following reaction conditions for the preparation of N-isopropyl-4-chloroaniline from p-nitrochlorobenzene and acetone are mentioned: reaction temperature 160° to 200° C., hydrogen pressure about 70 to 110 bar. Depending on the metal sulfide catalyst used, the reaction times are 15 minutes to 6.5 hours. The yields of N-alkylhalogenoaniline are 92.5 to 100%.

The two processes of the closest prior art mentioned have in common that the substrate used (halogenonitro aromatic or halogenoaniline) is reacted in a 15- to 10-molar excess of the carbonyl compound. As a result of the drastic reaction conditions employed, a significant portion of the carbonyl compound which is used as solvent is hydrogenated to the corresponding alcohol. This means, on the one hand, increased consumption of hydrogen, and, on the other hand, that the resulting alcohol/carbonyl compound mixture can only be separated by distillation with the use of large amounts of energy. Furthermore, the alcohol formed cannot be reintroduced into the continuous process cycle but has to be disposed of, for example, by introducing it into another process. Both processes have the additional disadvantage that they must be carried out at relatively high reaction temperatures to obtain acceptable reaction times and thus space-time yields.

In contrast, it has now been found that N-alkylhalogenoanilines of the general formula (I)

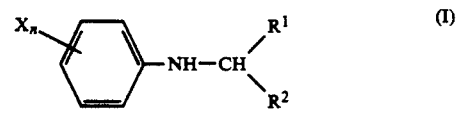

in which X is a chlorine or bromine atom and n is the number 1 or 2, $R^1$ is a linear or branched alkyl ($C_1$–$C_4$) radical, $R^2$ a linear or branched alkyl ($C_1$–$C_6$) radical or $R^1$ and $R^2$ together with the carbon atom to which they are bound can form a five- or six-membered cycloalkane ring, can be prepared in an advantageous manner, while avoiding the shortcomings of the known processes mentioned, by reacting a halogenonitrobenzene of the general formula (II)

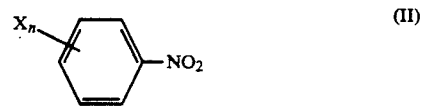

in which X and n have the abovementioned meanings with an at least stoichiometric amount of a carbonyl compound of the general formula (III)

in which $R^1$ and $R^2$ have the abovementioned meanings or $R^1$ and $R^2$ together with the carbon atom of the carbonyl group can form a five- or six-membered cycloalkane ring, in an organic solvent which is inert towards the reactants under the reaction conditions at temperatures of about 10° to about 100° C., preferably about 30° to about 50° C., at a hydrogen superatmospheric pressure of about 0 to about 50 bar, preferably about 5 to about 25 bar, in the presence of a sulfited platinum catalyst on activated carbon.

Examples of halogenonitrobenzenes of the general formula II mentioned, which can be used, are p-nitrochlorobenzene, o-nitrochlorobenzene, p-bromonitrobenzene, 2,5-dichloronitrobenzene, 3,4-dichloronitrobenzene, 3,5-dichloronitrobenzene, 2,4-dichloronitrobenzene or 2,3-dichloronitrobenzene.

Examples of suitable carbonyl compounds of the general formula III mentioned are acetone, diethyl ketone, methyl ethyl ketone, methyl isobutyl ketone, methyl isopropyl ketone, ethyl amyl ketone, ethyl isoamyl ketone, cyclopentanone or cyclohexanone. The carbonyl compounds are used in a one- to about 1.5-fold stoichiometric amount, relative to the halogenonitrobenzene. Although the use of a larger amount is possible, this does not have any additional positive effect but makes the process increasingly uneconomical.

Examples of inert solvents which can be used in the process according to the invention are methanol, ethanol, isopropanol, isobutanol, ethyl acetate, n-butyl acetate, isopropyl acetate, isoamyl alcohol or 2-ethylhexanol. Preferably, the reaction is carried out in alkyl acetates, such as ethyl acetate, n-butyl acetate or isopropyl acetate.

The platinum catalyst used in the process according to the invention is particularly important. It is a commercially available catalyst (DEGUSSA type F1OP, 5% by weight of platinum on activated carbon), which has been sulfited, i.e. deactivated, by a process described in German Patent 2,105,780. The catalyst is used in the process according to the invention in amounts of about 2 to about 10 percent by weight, preferably about 3 to about 5 percent by weight, relative to the halogenonitro compound. In serial tests carried out using the process according to the invention, the catalyst used is recycled up to 10 times without replenishing losses due to workup, its activity remaining constant.

Advantageously, the detailed procedure of the process according to the invention is as follows: 1 mole of a halogenated nitrobenzene is reacted in an inert organic solvent, preferably an alkyl acetate, such as, for example, ethyl acetate or in particular n-butyl acetate, over a sulfited platinum catalyst in the presence of an excess of about 20 mole percent of an aliphatic ketone of the formula III at a maximum temperature of 50° C. and a hydrogen pressure of about 5 to about 25 bar. After the reaction is complete, the platinum catalyst is filtered off, and the solvent used is distilled off in vacuo. The residue is fractionated in vacuo. The N-alkyl-halogenoanilines thus obtained usually have a purity of >99%. The catalyst used can be recycled without any loss in yield.

The advantages of the process according to the invention are a smaller amount of the aliphatic carbonyl compound used, a substantially lower reaction temperature in the reductive alkylation and an almost unlimited recycling of the solvent and catalyst used. In this process, except for the water of the hydrogenation reaction, no waste water is formed. Due to the low COD, the water formed by hydrogenation is highly biodegradable.

In the process according to the invention, the halogen elimination is 0 to not more than 1%, as detected by GC/MS. At reaction temperatures higher than 55° C. and also at higher hydrogen pressures such as, for example, 40 to 60 bar, considerably more halogen elimination was observed in some cases. For this reason, more drastic reaction conditions than the ones given are rather a disadvantage in the process according to the invention.

In principle, the reductive alkylation can also be carried out with the halogenoanilines which correspond to the halogenonitrobenzenes of the formula II. However, some of these aniline derivatives are hazardous due to their physiological properties, and require an additional process step for their preparation from the corresponding nitro compounds.

The N-alkylhalogenoanilines obtainable by the process are valuable starting materials and intermediates for the preparation of plant-protection agents and pharmaceuticals and valuable coupling components for the preparation of azo dyes.

The examples which follow are intended to illustrate the process according to the invention in more detail, without limiting it thereto.

EXAMPLE 1

2500 ml of n-butyl acetate and 397.7 g (2.5 mol) of technically pure p-nitrochlorobenzene and 175.7 g (3.0 mol) of acetone were initially introduced at room temperature into a 5-liter stainless steel hydrogenation autoclave. After the addition of 15.0 g of sulfited platinum catalyst (water content of the catalyst about 50%), the autoclave was flushed 3 times with nitrogen, and then 10 bar of hydrogen were injected at room temperature. The mixture was then hydrogenated at a temperature of <50° C. and a hydrogen pressure of 5 to 10 bar for about 1 hour. The hydrogen pressure was then increased to 25 bar, and stirring at 45° to 50° C. and a pressure of 20 to 25 bar was continued for 6 hours.

For workup, the autoclave was emptied and rinsed with 150 ml of n-butyl acetate, the catalyst was separated off through a filter and washed twice with 25 ml each of butyl acetate. The catalyst was moistened with 7.5 ml of water and stored for the next batch.

The filtrate was concentrated by distillation at about 13 mbar. The residue was then distilled in vacuo at 24 to 27 mbar through a packed column to give 372 g of N-isopropyl-4-chloroaniline, which distilled over at a boiling point of 122° to 127° C.

EXAMPLE 2

397.7 g (2.5 mol) of o-nitrochlorobenzene were reacted according to the procedure described in Example 1. The yield was 89% of theory at a purity of 99.0% (GC).

EXAMPLE 3

Analogously to Example 1, 397.7 g (2.5 mol) of p-nitrochlorobenzene were reacted in 2500 ml of ethyl acetate. The workup was carried out in principle analogously, except that the solvent was distilled off at atmospheric pressure and the residue was then likewise fractionated in vacuo.

EXAMPLE 4

Analogously to Example 1, 397 g (2.5 mol) of o-nitrochlorobenzene were reacted in 2500 ml of methanol. N-Isopropyl-2-chloroaniline was obtained by the workup described in Example 3 in a yield of 85% of theory at a purity of 98.7 [sic].

EXAMPLE 5

Comparison Example

Example 1 is repeated, except that the reductive alkylation is carried out at 100° C. and 40 to 60 bar hydrogen pressure, to give 344.0 g of N-isopropyl-4-chloroaniline, which corresponds to a yield of 70% of theory. In addition, 56.7 g of N-isopropylaniline are obtained, which is equivalent to a chlorine elimination of 14%.

EXAMPLE 6

480.0 g (2.5 mol) of 3,4-dichloronitrobenzene were reacted in 2500 ml of butyl acetate under the reaction conditions described in Example 1 with 10 g of sulfited platinum catalyst F1OP. After the solvent had been distilled off in vacuo, the residue was fractionated to give 431.0 g of N-isopropyl-3,4-dichloroaniline at a purity of 98.9% (GC) in the boiling range 143° to 148° C. (13.33 to 16 bar), which corresponds to a yield of 84.5% of theory.

In J. Amer. Chem. Soc. 87, 2767–2768, the suitability of the sulfides of platinum metals as catalysts in the hydrogenation of nitrobenzene to aniline is described. In addition, the further important use of the catalysts in question in the reduction of halogen-containing nitro compounds to give amines, without occurrence of dehalogenation, is mentioned there. It is additionally mentioned there that the sulfides of platinum metals can be used for the reductive alkylation of aliphatic amines or their nitroalkane precursors with aliphatic ketones.

We claim:

1. A process for the preparation of N-alkyl-halogenoanilines of the general formula (I)

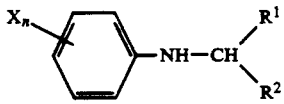 (I)

in which X is a chlorine or bromine atom and n is the number 1 or 2, $R^1$ is a linear or branched alkyl ($C_1$–$C_4$) radical, $R^2$ a linear or branched alkyl ($C_1$–$C_6$) radical or $R^1$ and $R^2$ together with the carbon atom to which they are bound can form a five- or six-membered cycloalkane ring, which comprises reacting a halogenonitrobenzene of the general formula (II)

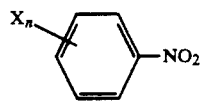 (II)

in which X and n have the abovementioned meanings with 1 to 1.5 times the stoichiometric amount of a carbonyl compound of the general formula (III)

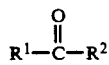 (III)

in which $R^1$ and $R^2$ have the abovementioned meanings or $R^1$ and $R^2$ together with the carbon atom of the carbonyl group can form a five- or six-membered cycloalkane ring, in an organic solvent which is inert towards the reactants under the reaction conditions at temperatures of 30° to 50° C., at a hydrogen superatmospheric pressure of about 0 to about 50 bar, in the presence of a sulfited platinum catalyst on activated carbon.

2. The process as claimed in claim 1, wherein the reaction is carried out at a hydrogen superatmospheric pressure of about 5 to about 25 bar.

3. The process as claimed in claim 1, wherein the reaction is carried out in the presence of 2 to 10 percent by weight of platinum catalyst on carbon, relative to the halogenonitrobenzene used.

4. The process as claimed in claim 1 wherein the reaction is carried out in the presence of 3 to 5 percent by weight of platinum catalyst on carbon, relative to the halogenonitrobenzene used.

5. The process as claimed in claim 1 wherein the halogenonitrobenzene used is p-nitrochlorobenzene, o-nitrochlorobenzene, p-bromonitrobenzene, 2,5-dichloronitrobenzene, 3,4-dichloronitrobenzene, 3,5-dichloronitrobenzene, 2,4-dichloronitrobenzene or 2,3-dichloronitrobenzene.

6. The process as claimed in claim 1 wherein acetone, diethyl ketone, methyl ethyl ketone, methyl isobutyl ketone, methyl isopropyl ketone, ethyl amyl ketone, ethyl isoamyl ketone, cyclopentanone or cyclohexanone is used as the carbonyl compound.

7. The process as claimed in claim 1 wherein the reaction is carried out in methanol, ethanol, isopropanol, isobutanol, ethyl acetate, n-butyl acetate, isopropyl acetate, isoamyl alcohol or 2-ethylhexanol as the solvent.

* * * * *